(12) United States Patent
Bock

(10) Patent No.: US 9,980,795 B2
(45) Date of Patent: *May 29, 2018

(54) SPATIALLY IMPROVED EXTENDED REACH ULTRASONIC TOOTHBRUSH

(71) Applicant: Robert T. Bock, Brewster, NY (US)

(72) Inventor: Robert T. Bock, Brewster, NY (US)

(73) Assignee: Robert T. Bock Consultancy LLC, Brewster, NY (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/085,753

(22) Filed: Mar. 30, 2016

(65) Prior Publication Data

US 2016/0206412 A1    Jul. 21, 2016

Related U.S. Application Data

(63) Continuation-in-part of application No. 14/556,190, filed on Nov. 30, 2014.

(51) Int. Cl.
| | | |
|---|---|---|
| A61C 17/20 | (2006.01) |
| A61C 17/34 | (2006.01) |
| A46B 15/00 | (2006.01) |
| A61C 19/06 | (2006.01) |

(52) U.S. Cl.
CPC .......... *A61C 17/20* (2013.01); *A46B 15/0028* (2013.01); *A61C 17/3481* (2013.01); *A61C 19/06* (2013.01)

(58) Field of Classification Search
CPC ..... A61C 17/20; A61C 17/3481; A61C 19/06; A46B 15/0028
See application file for complete search history.

(56) References Cited

U.S. PATENT DOCUMENTS

| | | | |
|---|---|---|---|
| 3,335,443 A | 8/1967 | Parisi | |
| 3,809,977 A | 5/1974 | Balamuth et al. | |
| 4,192,035 A | 3/1980 | Kuris | |
| 5,138,733 A | 8/1992 | Bock | |
| 5,369,831 A | 12/1994 | Bock | |
| 7,269,873 B2 * | 9/2007 | Brewer | A46B 15/0002 15/22.1 |
| 7,849,548 B2 * | 12/2010 | Bock | A46B 13/023 15/176.1 |

(Continued)

*Primary Examiner* — Joseph J Hail
*Assistant Examiner* — Henry Hong

(57) ABSTRACT

An ultrasonic toothbrush having spatially extended functionality to treat various oral diseases in addition to removing plaque and treating gingivitis is disclosed. In addition to the ultrasonically activated bristles, the toothbrush incorporates a multi directional ultrasound transducer system, which spatially irradiates the oral cavity with ultrasonic pressure waves, operational to loosen plaque, to remove periodontal bacteria from teeth and gums, and to simultaneously treat and destroy disease causing bacteria and bacterial chains on the inside surfaces of cheeks and lips, providing relief from Recurring Aphthous Stomatitis, Lichen Planus, and Mucositis. Various configurations are disclosed, including user removable and replaceable brush heads, ultrasound treatment heads, and a system of protecting the vibrating exposed ultrasound transducer from contacting the teeth of the user. A motorized version featuring sonic frequency orbital vibration brush head and bristle tufts is described.

8 Claims, 7 Drawing Sheets

(56) References Cited

U.S. PATENT DOCUMENTS

| | | | |
|---|---|---|---|
| 2002/0116775 A1* | 8/2002 | Wong | A61C 17/22 |
| | | | 15/22.1 |
| 2005/0091770 A1* | 5/2005 | Mourad | A46B 15/0002 |
| | | | 15/22.1 |
| 2008/0255498 A1* | 10/2008 | Houle | A61C 17/02 |
| | | | 604/20 |
| 2012/0137453 A1* | 6/2012 | Tsukino | A61C 17/20 |
| | | | 15/22.1 |
| 2013/0115571 A1 | 5/2013 | Emekci | |

* cited by examiner

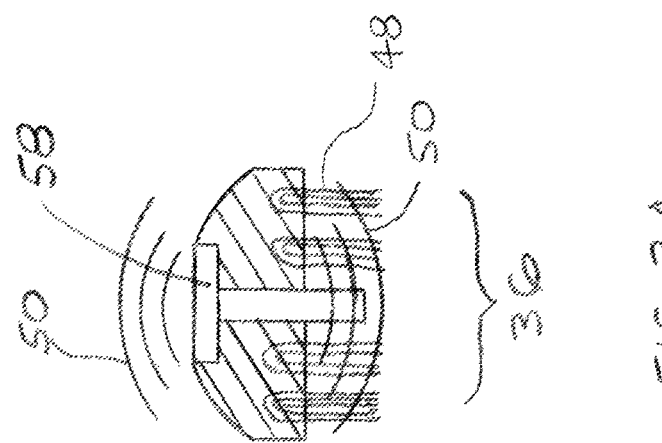
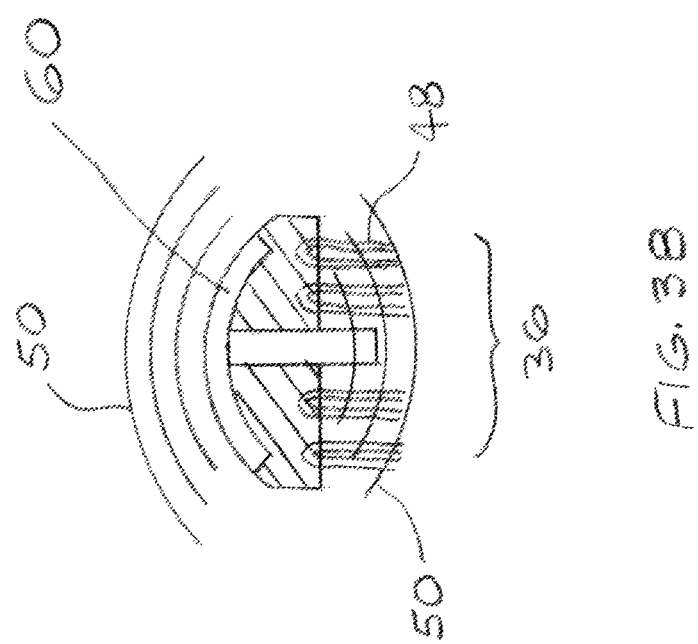

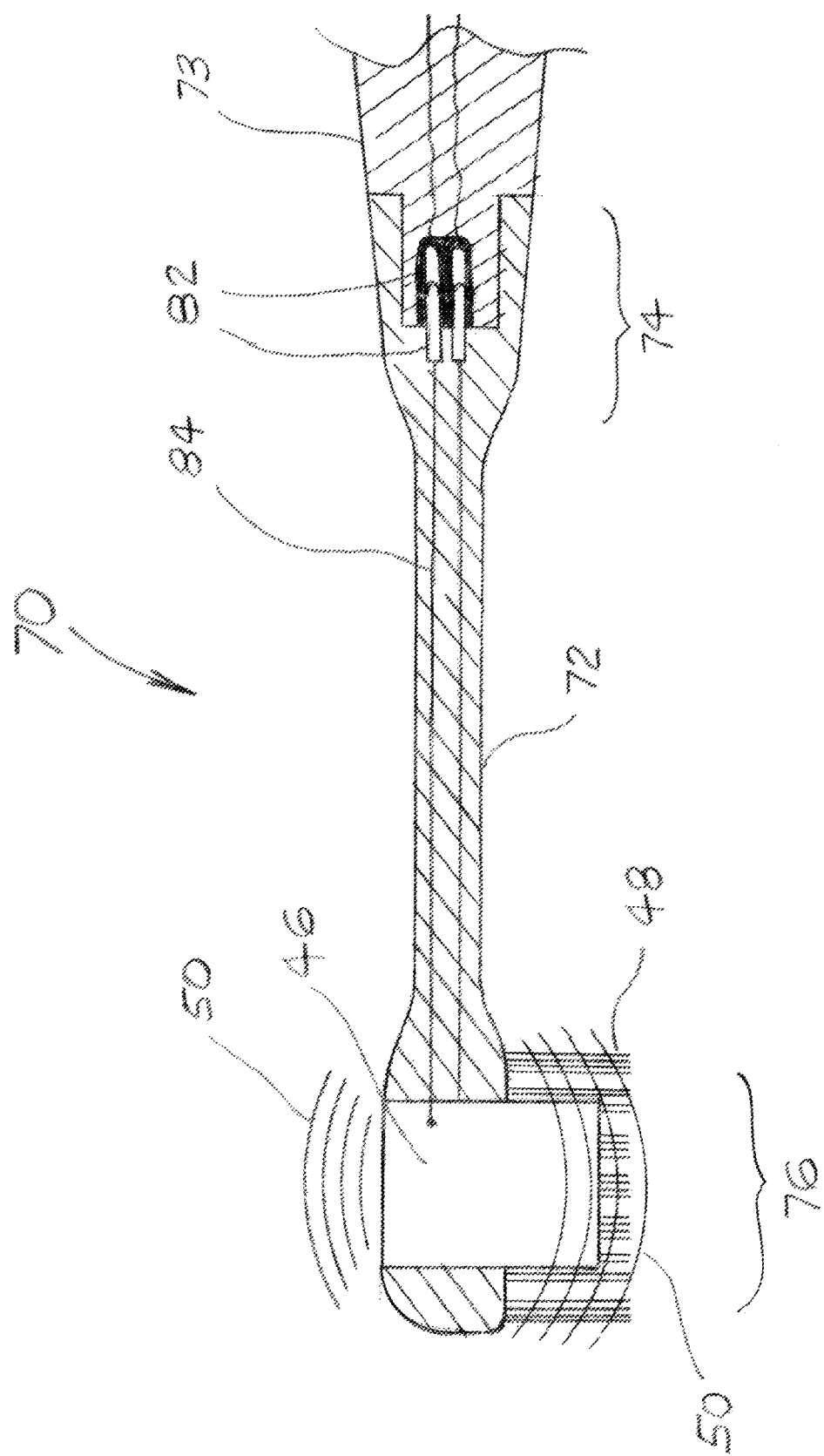

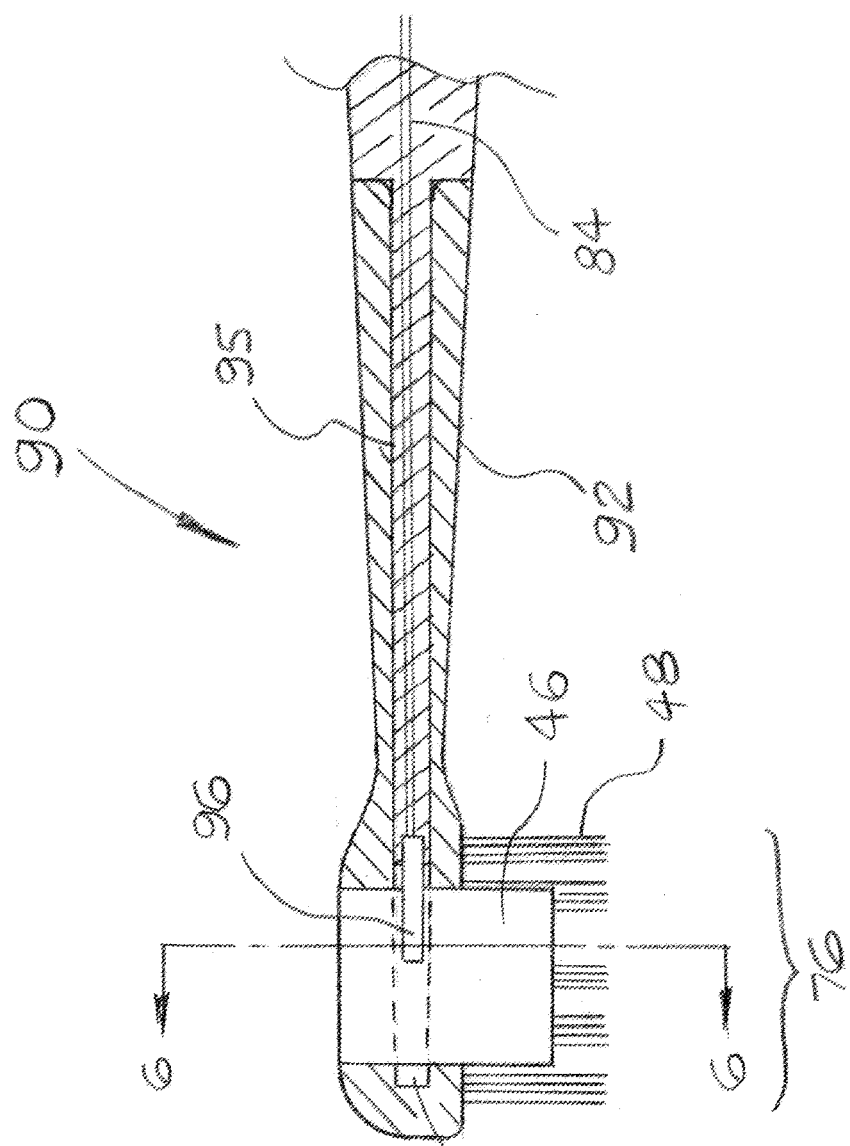
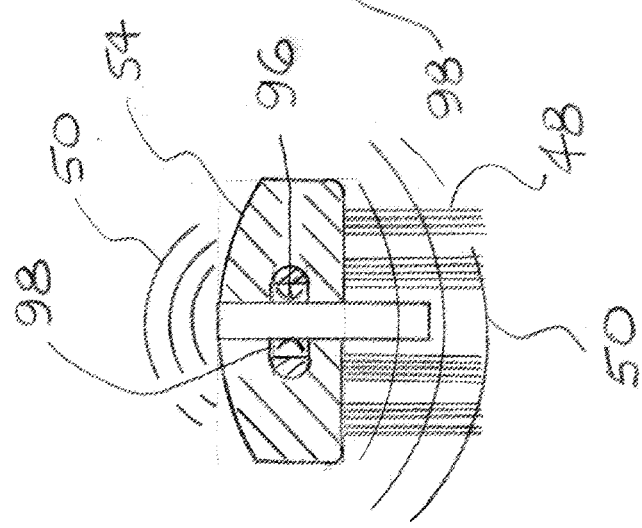
FIG. 5
FIG. 6

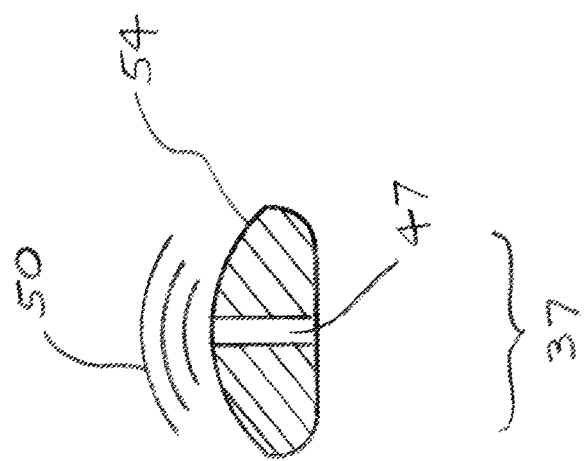
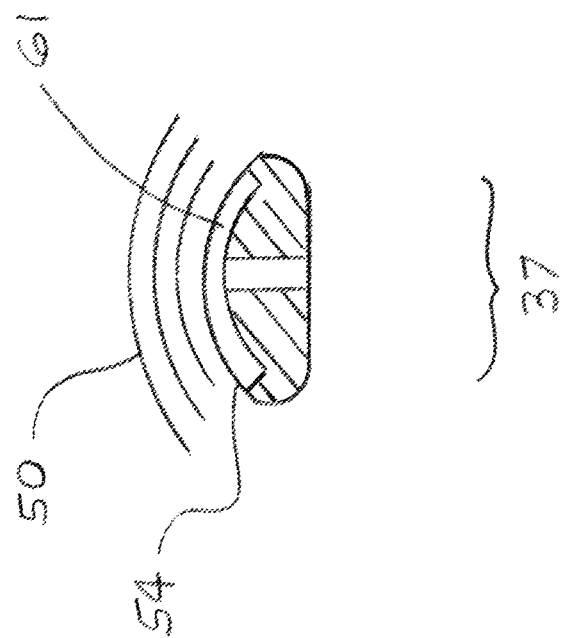

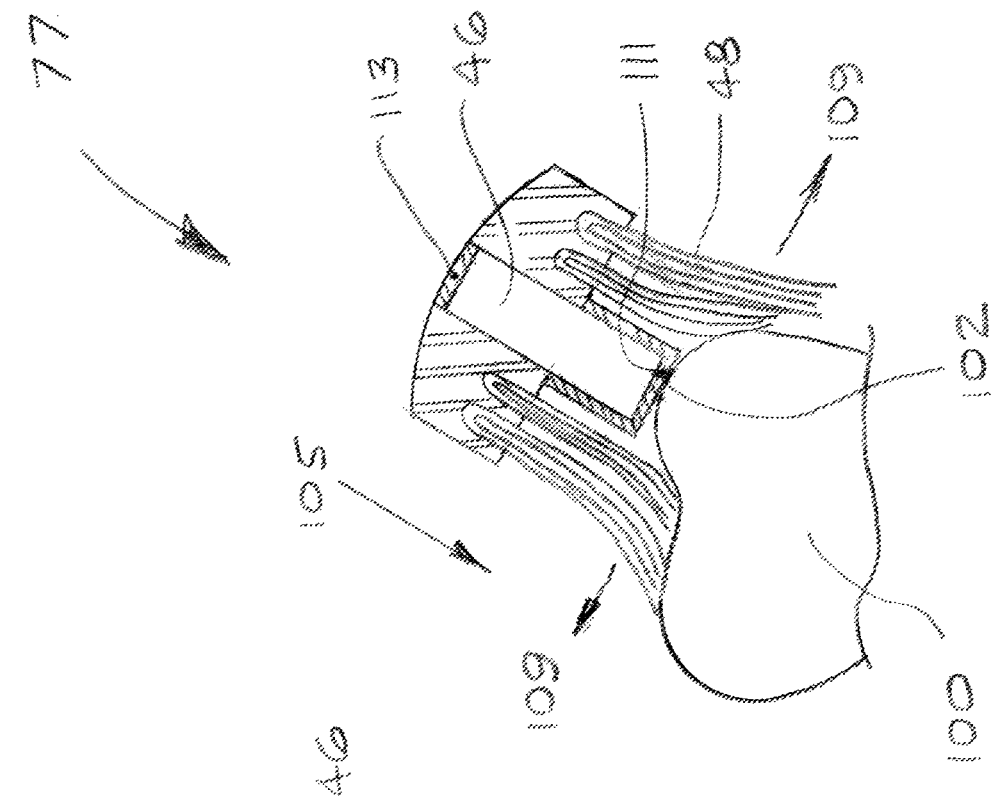
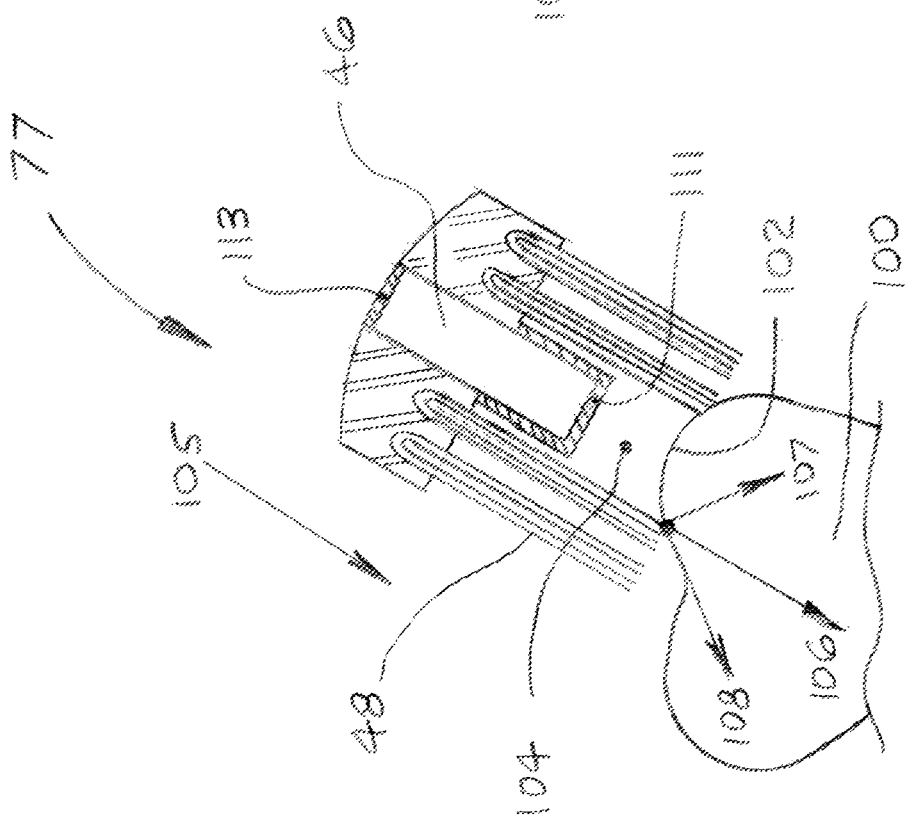

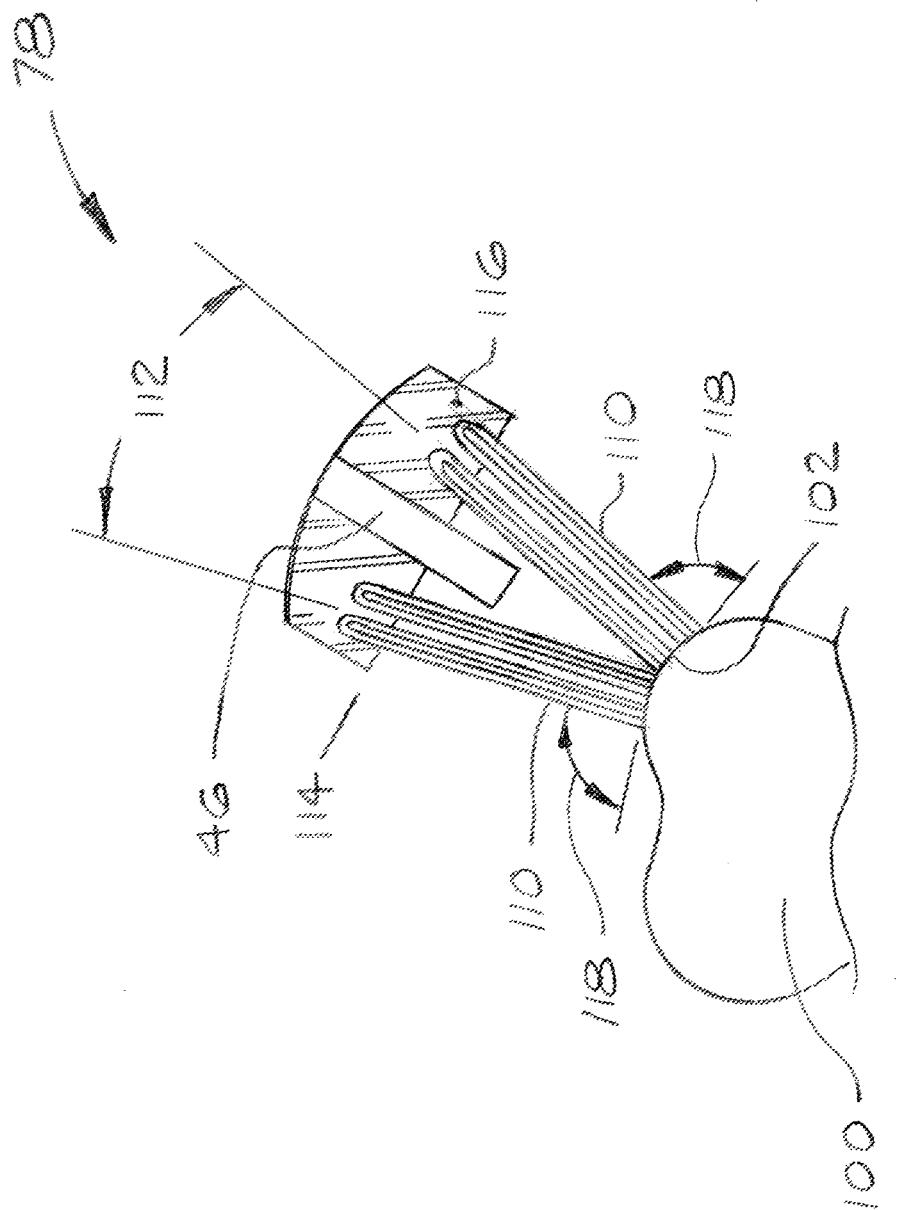

SPATIALLY IMPROVED EXTENDED REACH ULTRASONIC TOOTHBRUSH

CROSS REFERENCE TO RELATED APPLICATIONS

This is a Continuation-in-Part application of Ser. No. 14/556,190 filed Nov. 30, 2014, the contents of which are hereby incorporated by reference in their entireties as if fully set forth herein.

BACKGROUND OF THE INVENTION

1. Field of the Invention

This invention relates to toothbrushes and more particularly toothbrushes utilizing sonic and ultrasonic acoustic mechanism to increase the effectiveness of the toothbrushes and to provide for enhanced oral hygiene.

2. Description of Prior Art

Some of the early art of powered toothbrushes attempted to increase the speed of bristle vibrations by various sonic frequency and ultrasonic frequency means. These devices are exemplified by U.S. Pat. No. 3,335,443 by Parisi, U.S. Pat. No. 3,809,977 by Balamuth, and U.S. Pat. No. 4,192,035 by Kuris. These proposals did not utilize ultrasonic pressure waves to impact upon the plaque and periodontal bacteria on the teeth and gums; they were merely faster vibrating mechanical toothbrush designs. It is not known if any of these patents were utilized in commercially available toothbrushes.

The first commercially available ultrasonic toothbrush utilizing ultrasonic pressure waves to help remove plaque and destroy periodontal bacteria was based on U.S. Pat. No. 5,138,733 by Bock, which contained a piezoelectric transducer in the tip of the brush head to generate the ultrasonic pressure waves, which were transmitted through the bristles to teeth and gums. While this was a great leap forward in toothbrush design, it was not optimal since a significant portion of the ultrasound energy generated by the piezoelectric transducer were lost due to various structural ultrasound attenuation mechanisms. Material interfaces are not 100% efficient. Each material interface that the ultrasound wave has to travel through, such as the adhesive to transducer interface and the adhesive to housing interface securing the transducer in the housing, the housing to the brush head interface, and the brush head to the bristle interface are reflecting some of the ultrasound energy back toward the transducer. In addition, the long aspect ratio thin bristles attenuated some of the ultrasonic energy generated by the piezoelectric transducer. In both U.S. Pat. Nos. 5,138,733 and 5,369,831 also by Bock, the transmission of ultrasound toward the back of the brush head was also greatly reduced due to the numerous surface interfaces and thick housing materials, which attenuated the ultrasound energy toward the back side of the brush head. Nevertheless, U.S. Pat. Nos. 5,138,733 and 5,369,831 still represented the best solution for ultrasonic toothbrushes at their time.

U.S. Pat. No. 7,269,873 B2 by Brewer et. al, entitled "Ultrasonic toothbrushes employing an acoustic waveguide" represents the next technological improvement in the art. The Brewer patent is essentially a modification of U.S. Pat. No. 5,138,733 by Bock, wherein Brewer provides an improvement in the efficiency of the transmission of the ultrasonic pressure waves from the transducer through the toothpaste and the fluids in the mouth to the teeth and gums by the addition of a waveguide, which is more efficient in transmission of the ultrasonic waves toward teeth and gums than the bristles in U.S. Pat. No. 5,138,733 by Bock. However, the waveguide suggested by Brewer while more efficient than the bristles in Bock's disclosure and practice, still attenuates the ultrasonic energy produced by the transducer, both by the waveguide to transducer interfaces and the waveguide itself. In an attempt to maximize the ultrasonic energy output from the acoustic waveguide toward teeth and gums Brewer utilizes an ultrasound-reflecting element (see FIG.1 item 28) or an alternative air-gap (see FIG. 4) on the back of the ultrasound transducer. Air-gaps are known in the art to reflect and stop propagation of ultrasound pressure waves. Both the ultrasound reflecting element and the air-gap are isolating ultrasound wave emission from the back of the brush-head and from the lips and cheeks.

U.S. Pat. No. 7,849,548 B2 by Bock represents the next technological improvement in ultrasonic toothbrushes. In his disclosure Bock eliminates all structural attenuation of ultrasound energy emitted by the piezoelectric transducer toward teeth and gums by bringing the transducer out of the brush head and getting it in direct contact with the toothpaste and the fluids between the toothbrush and the teeth and the gums, greatly enhancing the efficiency and efficacy of the design. There are no surface interfaces or any other material to attenuate ultrasound energy between the transducer and the fluids of the oral cavity on the side of the bristles and teeth and gums. However, similarly to Brewer, Bock also proposed an ultrasound reflecting closed cell foam (see FIG. 1 item 40) on the back of the ultrasound transducer, which isolates ultrasound emission from the back of the toothbrush and the lips and cheeks.

Both U.S. Pat. No. 7,269,873 B2 by Brewer et. al, and U.S. Pat. No. 7,849,548 B2 by Bock disclose the heretofore standard construction techniques of the ultrasound transducer art throughout history, wherein the objective always has been to maximize ultrasound emission from the single "working" side of the transducer by the application of ultrasound reflecting materials and ultrasound reflecting air-gaps on the non-working "back" side of the transducer. This ultrasound emission maximization from the single working side significantly reduced and most often completely eliminated ultrasound emission from the non-working back side of the transducers.

The only known ultrasonic toothbrush in the prior art having an exposed ultrasound transducer is the U.S. Pat. No. 7,849,548 B2 by Bock. All other ultrasonic toothbrushes of the prior art, which are utilizing ultrasound transducers (see FIG. 1 of U.S. Pat. No. 5,138,733 by Bock, and FIG. 2 of US20130115571 A1 by Emecki) taught deploying the transducers inside of the plastic brush heads so they could not possibly come into contact with the user's teeth. It was discovered during the implementation of U.S. Pat. No. 7,849,548 B2 by Bock that the piezoelectric transducer exposed between the bristle tufts (see FIG. 7) does come into contact with the teeth when used by significant force in certain brushing sequences. Contacting the teeth, the vibrating piezoelectric transducer creates an uncomfortable sensation for the user, limiting utility of the device.

U.S. Patent Application US 20130115571 A1 by Emecki discloses a device wherein the toothbrush bristles are directly attached to one side of the transducer to act as waveguides and transfer the mechanical oscillation energy to the teeth. While Emecki does not describe the construction details of the brush head, it is clear from FIG. 2 of the disclosure that the mechanical oscillations are limited or completely eliminated by an air-gap or reflecting material on the back side of the transducer. Emecki's entire teaching and effort is focused on maximizing emission of mechanical oscillations into the bristles.

While progress to date was significant, the fact remains that the ultrasound toothbrush art has been focused on and only been successful to date to effectively remove plaque and periodontal bacteria from the teeth and gum surfaces.

Some people are suffering from various oral diseases, such as Recurrent Aphthous Stomatitis (RAS), commonly referred to as canker sores, Lichen Planus (LP) a chronic inflammatory disease with painful erosive or ulcerative areas mostly in the cheeks opposite to the teeth, and Mucositis (painful ulcerative lesions) caused by Anticancer Chemotherapy, which are appearing on the buccal and labial mucosa, the inside surfaces of the cheeks and the lips.

The ulcerative lesions of Mucositis are colonized by opportunistic bacterial micro organism, which create secondary infections making the already difficult to handle Chemotherapy process even less tolerable. There is evidence in the scientific community to support that RAS and LP are an aberrant immune response to the presence of oral flora. Thus a beneficial effect from the reduction in the oral bacterial load would be anticipated. Treatment with immunosuppressive agents, such as systemic or topical corticosteroids, will reduce RAS and LP activity in most patients with the disease. Unfortunately, this reduction is transient, and lesions quickly recur when treatment is discontinued. Because of the significant systemic side effects of corticosteroids, such as glaucoma, fluid retention, increased blood pressure, mood swings, osteoporosis, and more, the treatments with immunosuppressive corticosteroids cannot be tolerated for an extended period of time; the immunosuppressive corticosteroids treatments are only short-term temporary solutions. Therefore an effective therapeutic modality that is well tolerated for a long time would be of great value.

The ultrasonic toothbrush is a well-tolerated modality without any side effects. The limited amount of Ultrasound emitted from the backside of the first generation ultrasonic toothbrush based on U.S. Pat. No. 5,138,733 has been demonstrated by clinical studies to have a modest beneficial effect (46% reduction in the duration of RAS lesions as well as of decreasing the number of lesions that develop) on recurrent aphthous stomatitis. This modestly beneficial effect of the first generation ultrasonic toothbrush was limited by the structural attenuation of the ultrasonic pressure waves escaping through the backside of the brush head, contacting the inside surfaces of the lips and cheeks.

So, even the latest state of the art ultrasonic toothbrushes are not optimally efficient to attack and destroy the various oral bacteria residing and colonizing on the inside of the lips and cheeks opposite to teeth and gums, which are causative of RAS and LP.

The art is still missing the opportunity to conveniently and concurrently with removing plaque and periodontal bacteria from teeth and gums, also to provide relief of RAS and LP and improve the health status of people suffering from RAS and LP.

In summary, RAS and LP are both an aberrant immune responses related to oral flora, still waiting for an effective relief, by a well-tolerated modality, without immunosuppressive agents and their systemic side effects.

The ultrasonic toothbrush being a well-tolerated modality is a good candidate, but the quest for a multi purpose spatially highly effective device is still not fulfilled.

SUMMARY OF THE INVENTION

Responding to the above described needs the goals of this invention is to provide methods and devices, which in addition to removing plaque and periodontal bacteria from teeth and gums also effectively treat various oral health and hygiene problems, such as RAS and LP rooted in an aberrant immune response to the presence of oral flora on the lips and cheeks, and to provide relief from Mucositis by destroying the opportunistic bacterial micro organism colonizing in the Mucositis lesions, conveniently and concurrently with the daily tooth-brushing regimen.

The invention achieves these goals by the development and disclosure of the new methods and a new spatially improved ultrasonic toothbrush employing a high efficiency non-attenuated novel piezoelectric transducer mounting system wherein the transducer is exposed on two sides of the brush head. The piezoelectric transducer is exposed and protrudes between the bristles in direct contact with the toothpaste and the oral fluids toward teeth and gums to treat the periodontal bacteria and remove plaque from teeth and gums, and equally importantly, it is also exposed on the back of the brush head in direct contact with the oral fluids and with the inside surfaces of the lips and cheeks, delivering highly efficient non-attenuated ultrasound pressure waves to treat the oral flora and the tissues of the oral cavity opposite to teeth and gums. The intensity of these non-attenuated ultrasound pressure waves are more than double of the first generation ultrasonic toothbrush both on the bristle side and particularly on the back side of the brush head. Contrary to the temporary treatments of RAS and LP by immunosuppressive corticosteroids, the ultrasound modality is a well-tolerated long-term modality for years of daily application without limitation, providing long-term relief from RAS, LP, and Mucositis in a patient.

The new method comprises of the treatment of RAS, LP, and Mucositis lesions of the oral cavity by subjecting the oral flora colonizing in the lesions to ultrasonic pressure waves between 20 kHz and 20 MHz frequency, more typically within 750 kHz and 2 MHz frequency, at a non-attenuated intensity from 0.02 to 0.5 W/cm$^2$, more typically within 0.035 to 0.150 W/cm$^2$ either concurrently, in conjunction with, or independently of the daily tooth brushing regimen.

Accordingly, the new spatially improved ultrasonic toothbrush invention comprises a handle portion and a brush head portion. The brush head portion supports the bristle tufts and a piezoelectric ultrasound transducer, which is protruding from the head toward teeth and gums between the bristle tufts on one side and protruding though the head toward the internal surfaces of cheeks and lips on the opposite side of the bristle tufts. The handle portion contains a battery pack, an electronic motor to generate sonic frequency tactile vibrations of the brush head portion, an electronic control module to generate the ultrasonic frequency current to energize the ultrasound transducer and to provide control of the other functions in the toothbrush such as motor speed control, and battery charge control. The toothbrush system may also include a battery charging stand to provide the primary current for charging the battery in the handle, usually by conductive current means.

The ultrasound transducer being exposed directly to toothpaste and the dental fluid in the oral cavity on both sides of the brush head, in between the bristles on one side and opposite to the bristles on the other side is one of the major inventive steps of the invention. The direct exposure of the transducer to the dental fluids completely eliminates any structural attenuation of the ultrasound energy before it is transmitted to the dental fluids, the teeth and gums, and the surrounding surfaces of the dental cavity. An optional acoustic matching layer on the exposed surfaces of the transducer helps the coupling of the ultrasound energy through the propagation medium and the dental fluids in the mouth.

It has been shown in laboratory studies that without physical contact by the bristles even the highly attenuated ultrasound pressure waves emitted by the first generation ultrasonic toothbrush from a 5 mm distance through Brain Heart Infusion broth simulating gingival fluids (a) ruptured the Streptococcus Mutans bacterial chain, (b) reduced the thickness of the biofilm on the enamel surface, and (c) damaged the cell wall of Streptococcus mutans. The results showed that ultrasound also has some influence on Streptococcus mutans cell wall and intracellular components, suggesting that ultrasound inhibits the adherence of Streptococcus mutans on enamel surfaces. This is the mechanism that makes an enhanced removal of plaque possible by the bristles of the first generation ultrasonic toothbrush.

The present invention transmits more efficient and significantly higher intensity non-attenuated ultrasound pressure waves to tissues, generating mild cavitation in the fluids of the oral cavity. In combination with the dynamic fluid motion generated by the sonic frequency bristle vibration, the invention significantly improves the ability of the toothbrush to remove substantially all plaque from teeth and gum surfaces and to destroy bacterial colonies further beyond the reach of the bristles by as much as 7 to 10 mm in between teeth and into periodontal pockets.

The invention's non-attenuated ultrasound pressure waves from the back side of the brush-head treat, damage, interrupt and disorganize the bacterial colonies residing on the inside surfaces of the cheeks and lips of the oral cavity, mitigating the effects of RAS and LP and Mucositis to the extent that was not previously possible in the art.

Another objective of the invention is to overcome a critical fault in the prior art wherein the exposed ultrasound transducers were allowed to contact the teeth of the user creating an uncomfortable sensation. The present invention provides an alternative construction having a protective layer of bristle tufts projecting on the top of the exposed transducer and preventing the exposed transducer from contacting the teeth.

The invention, without any extra effort by the user, extends the daily tooth-brushing regimen into a previously unavailable complete oral hygiene regimen.

BRIEF DESCRIPTION OF THE DRAWINGS

FIGS. 3A and 3B shows multi element transducer configurations to extend non-attenuated transducer contact areas with the mucosa.

FIG. 4 shows side cross sectional view of a removable brush head assembly.

FIG. 5 and FIG. 6 show two cross sectional views of another embodiment of a removable brush-head assembly.

FIG. 7 and FIG. 8 shows two cross sectional views of two embodiments of an ultrasound applicator head assembly.

FIG. 9A and FIG. 9B show cross sectional views of the brush head having an exposed ultrasound transducer and state of art bristle configurations.

FIG. 10 shows a cross sectional view of a brush head incorporating a protection of the exposed ultrasound transducer by a unique bristle tuft configuration wherein the bristle tufts are projecting over the top of the transducer preventing the transducer from contacting the teeth.

DESCRIPTION OF THE PREFERRED EMBODIMENTS

In the title and in the following discussion the term "spatially improved" refers to the multi-directional effectiveness of an ultrasonic toothbrush in space versus the prior art ultrasonicl toothbrush, which is effective only on one side toward the bristles.

The term "ultrasound" and "ultrasonic" and "ultrasonic pressure waves" refer to acoustic energy in either continuous wave ultrasound or repetitive burst type ultrasonic modality having an operating frequency of 20 kHz and above. References made to "sonic" and "sonic vibrations" utilized in toothbrushes are referring to physical vibrations or oscillating motions significantly below the 20 kHz ultrasonic threshold, typically in the range of 100 to 500 Hertz. The term "cavitation" in association with the toothbrush refers to the generation and/or dispersion of bubbles and the interaction between the sonic or ultrasonic energy and vibrations with the bubbles within the oral fluidic environment. The term "structural attenuation" in association with ultrasound refers to the attenuation effects of the various surface interfaces and materials commonly used for housing the ultrasound transducers and for transmitting ultrasound from the transducer to the anatomy in ultrasonic toothbrushes and other ultrasonic applications.

The damaging effects of ultrasound on bacteria and bacterial colonies and rendering bacterial colonies ineffective are well known and documented in the scientific community. Clinical and laboratory studies of earlier generation ultrasonic toothbrushes cited herein are only a small set of examples of the effectiveness of the ultrasound emitted by the toothbrush on the bacterial colonies and plaque. It is well known that the effectiveness of ultrasound is related to the intensity of the application, so it is important to limit energy losses and maximize the available intensity from an ultrasound transducer within the limitation of the tissue-heating threshold.

Figure 1:
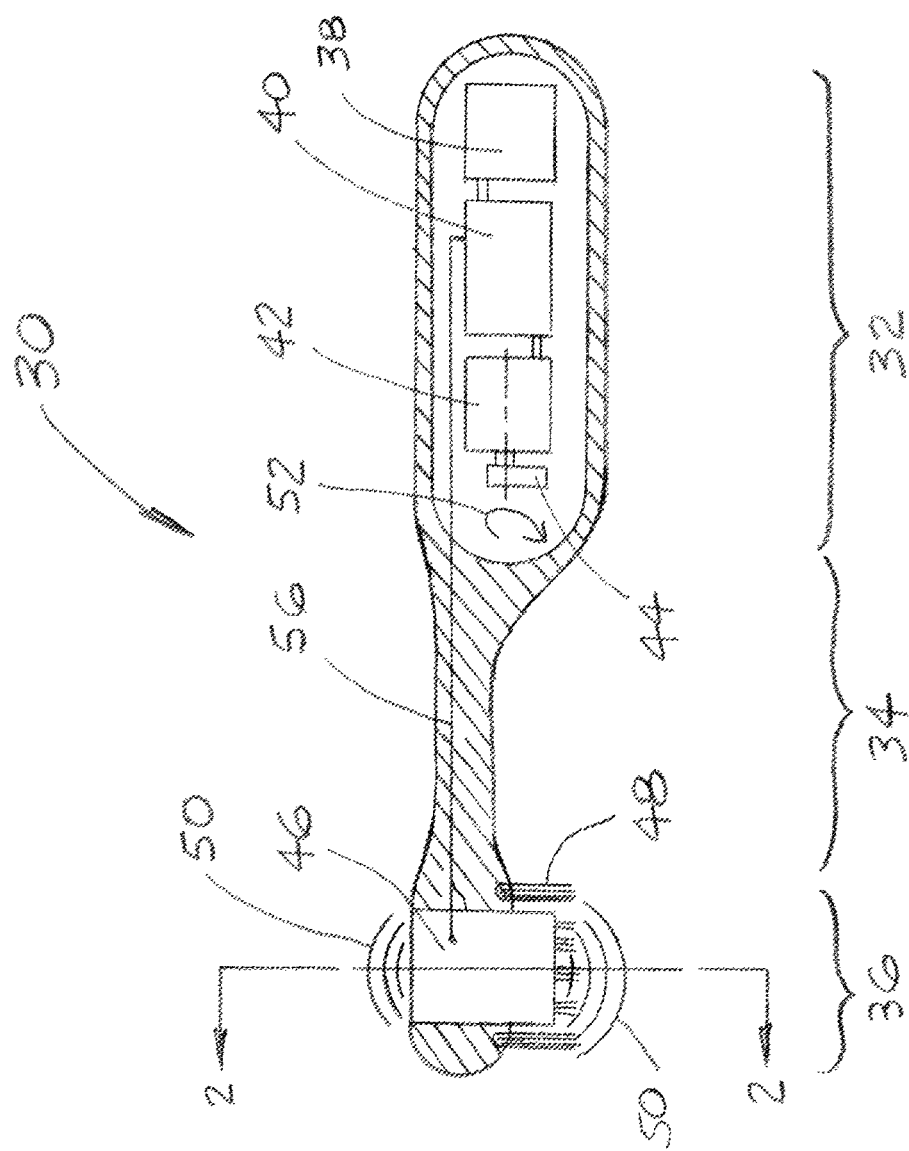
FIG. 1 shows a longitudinal cross section and a schematic of the invention consisting the brush head portion incorporating the tufts of bristles and the exposed ultrasonic transducer, and the handle portion containing the driving motor, electronic controls and a battery.
Figure 2:
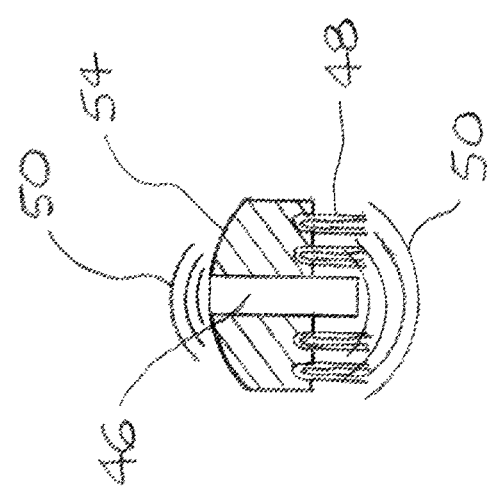
FIG. 2 shows the cross section of the brush head and exposure of the non-attenuated piezoelectric ultrasound transducer.

The invention of the spatially improved extended reach ultrasonic toothbrush 30 in a preferred configuration is shown in FIG. 1 and FIG. 2. The toothbrush 30 comprises of a handle portion 32, a neck portion 34, and a brush-head portion 36 constructed of a rigid or semi rigid plastic material. The handle portion 32 contains a battery pack 38, an electronic control module 40, and an electric motor 42 with an off-center weight 44 mounted on the shaft of the motor 42. The brush-head portion 36 contains an ultrasound transducer 46 and one or more bristle tufts 48.

The battery pack 38 is typically a multi-cell rechargeable battery of NiCd or NiMH chemistry system providing approximately 4.8 VDC to the electronic control module 40. The electronic control module 40 has multiple functions. It controls the electric motor 42 to produce various speed sonic frequency orbital vibrations 52 typically between 100 Hz and 500 Hz to the preference of the user, or no vibration when the application calls for the toothbrush to emit only ultrasonic pressure waves 50 without sonic frequency bristle vibrations. The electronic control module 40 generally will boost the battery voltage by a voltage multiplier circuit to the range of 9.6 VDC to 16.0 VDC in conjunction with generating the ultrasonic frequency current between 20 kHz and 20 MHz frequency, more typically within 750 kHz and 2 MHz frequency, for energizing the ultrasound transducer 46.

The brush-head portion 36 houses the bristle tufts 48 and the ultrasound transducer 46. The ultrasound transducer 46 is positioned within and protrudes from the brush-head 36 in two directions to provide spatial radiation of ultrasound pressure waves 50 without any structural attenuation of the spatially radiating ultrasound energy.

The transducer 46 protrudes from the brush-head 36 between the bristle tufts 48 toward teeth and gums on one side and protrudes though the brush-head 36 on the opposite side of the bristle tufts 48 toward the internal surfaces of the cheeks and lips.

The transducer 46 is typically constructed of one or more elements of hard piezoelectric materials, such as PZT-4 or PZT-8 Lead Zirconate Titanate composition ceramics. The PZT-4 material is a particularly good candidate for the toothbrush application since it is capable of producing large mechanical drive amplitudes while maintaining low mechanical and dielectric losses. However various other transducer materials are also available in the art, such as single crystal silicones, capacitive micro-machined materials, electrostatic polymers, and more will be available in the future to construct an ultrasonic transducer. When energized by the ultrasonic frequency current supplied by the electronic control module 40 through the interconnecting wiring 56 to the ultrasound transducer 46 the transducer 46 expands and contracts in tune with the ultrasonic frequency current, producing and transmitting ultrasound pressure waves 50 spatially into the surrounding and contacting materials, the toothpaste, the oral fluids, and the tissues of the oral cavity. To assure the best possible intimate contact with and transmission of the non-attenuated ultrasound pressure waves 50 into the lips and the cheeks, the brush head surface 54 opposite to the bristles 48 is constructed with a curved configuration and the ultrasound transducer is exposed at the peak of this surface. While FIG. 2 depicts the simplest transducer configuration constructed of a single element, other advanced multi-element configurations are possible.

FIG. 3A depicts a two-element straight "T" shape ultrasound transducer 58 while FIG. 3B depicts a curved "T" shape ultrasound transducer 60 illustrative of numerous configurations possible to increase contact areas with the mucosa of the lips and cheeks to further widen the spatial feature of the ultrasonic toothbrush, and not to miss the sometimes small but painful lesions of RAS and LP and Mucositis.

FIG. 4 depicts a removable brush-head assembly configuration of the invention. The removable brush-head assembly 70 comprises a substantially rigid elongated structural member 72 having a base portion 74 designed for secure attachment to a mating 73 portion of the toothbrush handle, a brush-head portion 76 housing one or more bristle tufts 48 and an ultrasound transducer 46. The ultrasonic frequency power to energize the transducer 46 is provided by an ultrasonic frequency current generator located in the toothbrush handle through a connector set 82 and connecting wiring 84.

The ultrasound transducer 46 protrudes from the brush-head portion 76 in two directions to provide spatial radiation of ultrasound pressure waves 50 without any structural attenuation of the ultrasound energy. The transducer 46 protrudes from the brush-head 76 between the bristle tufts 48 on one side and protrudes though the brush-head 76 on the opposite side of the bristle tufts 48.

FIG. 5 and FIG. 6 depict another embodiment of a removable brush-head assembly 90. In this embodiment the brush-head assembly 90 comprises a substantially rigid elongated tubular stem 92, which slides over and secures on a mating shaft 95 of the toothbrush handle, a brush-head portion 76 housing one or more bristle tufts 48 and an ultrasound transducer 46. The ultrasonic frequency power to energize the transducer 46 is provided by an ultrasonic frequency current generator located in the toothbrush handle connecting through a spring loaded sliding connector set 96 located in a slot 98 in the tip of the mating shaft 95 and connecting wiring 84.

The ultrasound transducer 46 protrudes from the brush-head portion 76 in two directions to provide spatial radiation of ultrasound pressure waves 50 without any structural attenuation of the ultrasound energy. The transducer 46 protrudes from the brush-head 76 between the bristle tufts 48 on one side and protrudes though the brush-head 76 on the opposite side of the bristle tufts 48.

FIG. 7 depicts a cross section of a removable ultrasound applicator head assembly 37 configuration of the invention, having a one-element ultrasound transducer 47. The removable ultrasound applicator head assembly 37 has an identical construction as the removable brush-head assemblies 70 and 90 shown in FIG. 4 and FIG. 5 respectively, with the exception that the removable ultrasound applicator head assembly 37 does not contain any bristles. All construction notes contained in the descriptions of FIG. 4 and FIG. 5 of the removable brush-head assemblies 70 and 90 are applicable to the removable ultrasound applicator head assembly 37 with the exception of references to the bristles.

The purpose of the removable ultrasound applicator head assembly 37 is to provide an optional accessory for the ultrasonic toothbrush to apply non-attenuated ultrasound treatment for RAS, LP, or Mucositis lesions at any time, independently from the daily tooth-brushing regimen. The ultrasound transducer 47 is exposed at the peak of the curved surface 54 of the applicator head assembly 37 and the ultrasound pressure waves 50 are conducted from the non-attenuated transducer to the bacterial flora by the oral fluids without the need for toothpaste.

FIG. 8 depicts a cross section of a removable ultrasound applicator head assembly 37 having a curved two-element ultrasound transducer 61 adopted to increase the contact surface between the transducer 61 and the lesions in the oral cavity. All other construction notes of FIG. 7 are applicable to FIG. 8 also.

FIG. 9A and 9B show cross sections of a brush head portion 77 of a removable brush-head assembly 70. The removable brush-head assembly 70 is not shown in these FIGS. 9A and 9B but described in details in the notes attached to FIG. 4. Brush head portion 77 utilizing conventional bristle tufts 48 of the prior art configuration positioned in parallel with and surrounding the ultrasound transducer 46 in a brushing position on a tooth 100 is shown in FIG. 9A. As taut in the prior art, bristle tufts 48 are spaced around transducer 46 leaving a significant gap 104 between tufts 48 where tufts 48 contact the crown 102 of teeth 100. The user approaches the tooth 100 in the direction indicated by arrow 105. When the user brushing the tooth 100 with a gentle touch, bristle tufts 48 space the ultrasound transducer 46 apart from the crown 102 of tooth 100. However, as illustrated, tufts 48 of the prior art are not touching the crown 102 squarely, but on an angle. Therefore, the brushing force 106 applied by the user against the angled surfaces of the crown 102 consist of two vector forces, vector force 107 perpendicular to the surface of the crown 102 and vector force 108 parallel with the surface of the crown 102. Vector force 107 does the majority of the plaque removing scrubbing of the crown 102 while vector force 108 tends to bend the bristles away from the perpendicular position, reducing the effectiveness of the bristles. As the user increases brushing force 106 in direction 105, both vector force 107 and vector force 108 increase proportionately. Also shown in FIG. 9A and 9B are optional sub millimeter thickness non-attenuating FDA food grade coating 111 and 113 on the otherwise exposed surfaces of the ultrasound transducer 46 to seal in any possible lead or other harmful contamination, when they are present in the transducer utilized in the design.

FIG. 9B demonstrates the displacement of bristle tufts 48 due to the vector forces, particularly vector force 108. As the user applies an increasing brushing force in direction 105 on the corners of the crown 102 of tooth 100, the conventional bristle tufts 48 will slide around the corners of the crown 102 and spread out in a lateral direction 109. As bristles 48 spread out in directions 109 they are allowing the transducer 46 to come into contact with the corner of the crown 102 resulting in an uncomfortable feeling for the user. This uncomfortable feeling can be highly significant when the electric motor of the toothbrush is activated and producing orbital vibration of the brush head portion 36. Therefore, it is desirable to prevent the transducer 46 to come into contact with the corner of the crown 102.

FIG. 10 shows an alternative embodiment of the invention wherein the exposed ultrasound transducer 46 is protected and prevented from touching the teeth 100. The invention shown in FIG. 10 depicts a bristle tuft 110 configuration which extends over the top of transducer 46 to prevent the transducer 46 to come into contact with the corner of the crown 102 of tooth 100 versus the conventional parallel bristle configuration of the prior art (see U.S. Pat. No. 7,849,548 B2 by Bock) which did not cover the transducer 46. The bristle tufts 110 are protecting the transducer 46 and preventing it to touch the crown 102 of teeth 100 by two methods. First, in this new configuration the bristle tufts 110 are placed in a converging 112 configuration around the transducer 46 to protrude directly in the front of the transducer 46. Being positioned between transducer 46 and the teeth 100 bristle tufts 110 are physically preventing transducer 46 to come in contact with teeth 100. Secondly, as the bristle tufts 110 are positioned substantially perpendicular 118 to the curvature of the crown 102 of teeth 100, the dynamic bristle spreading the vector forces (described in the notes attached to FIG. 9A) are eliminated, which prevents the bending of the bristle tufts 110 out of their position from between transducer 46 and the crown 102 of teeth 100.

All of the patents and publications cited herein and in the appended Information Disclosure Statement are hereby incorporated by reference in their entireties.

While the preceding description contains numerous specificities, these should not be construed as limitations on the scope of the invention, but rather as an exemplification of a preferred and additional embodiments thereof. Skilled artisans will readily be able to change dimensions, shapes, and construction materials of the various components described in the embodiments and adopt the invention to all types of sonic and ultrasonic energy applications. Accordingly, the scope of the invention should be determined not by the embodiments illustrated, but by the appended claims and their legal equivalents.

What is claimed:

1. An ultrasonic toothbrush comprising:
    a) a brush head portion having multiple bristle tufts composed of a plurality of bristles and at least one ultrasound transducer protruding from said brush head portion between the bristles on one side and mounted flush with said brush head on a opposing side, radiating non attenuated ultrasound pressure waves in multiple directions toward teeth and gums on one side, and toward an inside surfaces of cheeks and lips of a oral cavity on a other side, and coupling said non attenuated ultrasound pressure waves by a dentifrice and fluids in the oral cavity simultaneously in said multiple directions to the teeth and gums and said inside surfaces of cheeks and lips;
    b) portions of said multiple bristle tufts extending over a top of said protruding ultrasound transducer preventing physical contact between said transducer and teeth of user;
    c) a handle portion containing means generating ultrasonic frequency electronic current and connecting means of said ultrasonic frequency electronic current to energize said ultrasound transducer located in said brush head portion;
    d) said brush head portion is removable from said handle portion and includes means to securely connect said brush head portion to said handle portion and means to connect said ultrasonic frequency electronic current from said handle portion to power said ultrasound transducer within said brush head portion.

2. The ultrasonic toothbrush of claim 1, wherein said non attenuated multi-directional ultrasound pressure waves radiated by said transducer are operating between 20 kHz and 20 MHz frequency and intensity of 0.02 to 0.5 W/cm$^2$.

3. The ultrasonic toothbrush of claim 1 or 2, wherein the said multi-directional and non-attenuated ultrasound pressure waves radiated by said transducer are operative to damage and reduce effectiveness of disease causing bacteria and bacterial colonies in the oral cavity.

4. The ultrasonic toothbrush of claim 1, wherein an exposed radiating surfaces of said ultrasound transducer incorporate a sealant coating preventing any harmful component of said ultrasound transducer to propagate from said ultrasound transducer to the human anatomy.

5. The ultrasonic toothbrush of claim 1 or 2, wherein the ultrasound transducer comprises at least two transducer elements radiating said ultrasound pressure waves, one said transducer element radiating toward said teeth and gums, another said transducer element radiating toward the inside surfaces of the cheeks and lips of the oral cavity.

6. The ultrasonic toothbrush of claim 1, additionally comprising a motor secured to a structure of said handle portion having means to generate orbital vibrations of said handle portion and said brush head portion.

7. The ultrasonic toothbrush of claim 6, wherein a frequency of said orbital vibrations is between 100 Hz and 500 Hz.

8. The ultrasonic toothbrush of claim 6, further comprising means to selectively generate orbital vibrations or not to generate said orbital vibrations of said handle portion and said brush head portion while maintaining emission of said ultrasound pressure waves according to the desires of the user.

* * * * *